United States Patent [19]

LeVeen

[11] 4,256,768

[45] Mar. 17, 1981

[54] TREATMENT WITH DIALDEHYDES

[76] Inventor: Harry H. LeVeen, 800 Poly Pl., Brooklyn, N.Y. 11209

[21] Appl. No.: 24,028

[22] Filed: Mar. 26, 1979

Related U.S. Application Data

[63] Continuation of Ser. No. 863,443, Dec. 22, 1977, abandoned, which is a continuation of Ser. No. 680,714, Apr. 27, 1976, abandoned, which is a continuation-in-part of Ser. No. 678,955, Apr. 21, 1976, abandoned.

[51] Int. Cl.³ ............................................. A61K 31/11
[52] U.S. Cl. ................................................... 424/333
[58] Field of Search ......................................... 424/333

[56] References Cited

PUBLICATIONS

Chemical Abstracts 56:7932(6), (1962).
Chemical Abstracts 80:6775c, (1974).

*Primary Examiner*—Jerome D. Goldberg
*Attorney, Agent, or Firm*—Brooks, Haidt, Haffner & Delahunty

[57] ABSTRACT

Lower aliphatic dialdehydes have been found to react with human and other animal tissues in the living animal and that treatment of exposed tissue by topical application is useful in converting "wet" gangrene to "dry" gangrene. Treatment is generally by topical application of the dialdehyde diluted, typically, to 1 or 2 percent in a fluent carrier such as water or alcohol.

7 Claims, No Drawings

TREATMENT WITH DIALDEHYDES

RELATED APPLICATION

This application is a continuation of LeVeen Application Ser. No. 863,443, filed Dec. 22, 1977 now abandoned which is a continuation of LeVeen application Ser. No. 680,714, filed Apr. 27, 1976, now abandoned, entitled *TREATMENT WITH DIADELDYDES*, which is in turn a continuation-in-part of LeVeen application Ser. No. 678,955, filed Apr. 21, 1976 now abandoned, entitled *TREATMENT WITH GLUTARALDEHYDE*.

This invention relates to the treatment of human and other animal tissue of a living animal and in particular provides a process for treating the surface of exposed tissue to alter the nature of the tissue in a manner having beneficial results in a variety of applications.

One important object of the present invention is to provide a process for treating "wet" gangrene in order to convert it to "dry" gangrene.

It is a further object of this invention to provide a process for the treatment of burns which will promote the healing of the burns, and which in the case of extensive burns such as third degree burns, can assist in lowering the fatality rate.

These and other objects of the present invention are obtained by topical application to the exposed surface of the tissue to be treated with lower aliphatic dialdehydes diluted in a suitable, pharmaceutically acceptable carrier and is based on the discovery that such dialdehydes, although moderately toxic and irritating, when suitably diluted will effectively and safely react with animal tissue in the living animal to alter its nature in a way promoting the above objects. It has also been found that aliphatic dialdehydes have germicidal and sporicidal properties which are consistent with the above objects.

It has heretofore been known that glyoxal and gluteraldehyde will cause cross-linking of protein molecules to convert them to a stable polymer. Apparently, the same chemical reactions take place with human and other animal tissue in the living animal.

In accordance with the present invention, the application of the dialdehyde is made directly and topically to the surface of the tissue to be treated, suitably diluted in a pharmaceutically acceptable carrier from 0.1% up to about 10% by weight of the dialdehyde. Preferably, the dilution is on the order of 1 or 2% for topical application to exterior portions of the body and 1% where the application is to surgically exposed internal parts of the body.

Gluteraldehyde is infinitely soluble in water and ethyl alcohol, and the preferred pharmaceutical carriers for it are water and water/alcohol mixtures such as 70% ethyl alcohol. For internal application, the preferred carriers are water and saline.

Glyoxal, which is very soluble in water, is also preferably diluted in water or saline as a carrier. Glyoxal is available commercially in 40% aqueous solutions which contain a polymerization inhibitor and can be used simply by diluting further with water.

Succinaldehyde, which is only slightly soluble in alcohol and water and adipaldehyde, which is insoluble in water but very soluble in alcohol, can be used in aqueous systems as suspensions, but also where continuous application is desired can be incorporated in ointments and the like. The relatively water-insoluble dialdehydes have the additional advantage in that tissue penetration is limited and the possibility of toxicity problems is thereby reduced.

Treatment of Gangrene

A smelly, infected ischemic ulceration of the foot is treated by a continuous soak of the infected area with a 1% solution of gluteraldehyde either in water or in 70% ethyl alcohol until the ulceration is converted to a dry, coagulation type of necrosis that is seen when the arterial blood supply of an extremity is compromised without infection. In this situation, the gangrenous part can frequently be left for auto-amputation. Active infection of an ischemic extremity ordinarily requires amputation at a considerably higher level in the limb in order to rid the body of infection and assure that the amputation is performed through healthy, viable tissue capable of healing. The conversion of "dry" gangrene, on the other hand, is like the coagulation necrosis which occurs with arterial insufficiency unassociated with infection. This is especially important in diabetic gangrene, where "moist" gangrene is frequently encountered because of the lowered resistance of diabetics to infection.

Treatment of Burns

Burned and weeping tissue is converted to a leather-like eschar which is intimately attached to the underlying tissue by the application to the surface of the burn of a 2% solution of gluteraldehyde in water. Application is made topically with a continuous soak until the protective eschar is formed. As epitheiazation takes place, the eschar is lifted and drops off in the same manner as a natural scab. Application in this manner with third degree burns in mice has been found to lower the fatality rate in extensive body burns.

Other lower aliphatic dialdehydes such as glyoxal, succinaldehyde, adipaldehyde, and suberaldehyde are substituted for gluteraldehyde with similar results.

I claim:

1. A method of treating wet gangrenous tissue in a living animal which comprises applying to the surface thereof a lower aliphatic dialdehyde selected from the group consisting of glyoxal, glutaraldehyde, adipaldehyde, succinaldehyde, and suberaldehyde diluted from 0.1% up to about 10% by weight in a pharmaceutically acceptable carrier until said wet gangrenous tissue is converted to dry gangreneous tissue.

2. A method according to claim 1 in which the proportion of dialdehyde is up to 10% by weight of the carrier.

3. The method according to claim 1 in which the dialdehyde is gluteraldehyde.

4. The method according to claim 1 in which the dialdehyde is succinaldehyde.

5. The method according to claim 1 in which the dialdehyde is glyoxal.

6. The method according to claim 1 in which the dialdehyde is adipaldehyde.

7. The method according to claim 1 in which the dialdehyde is suberaldehyde.

* * * * *